(12) United States Patent
Muhanna et al.

(10) Patent No.: US 6,585,769 B1
(45) Date of Patent: *Jul. 1, 2003

(54) ARTIFICIAL SPINAL LIGAMENT

(75) Inventors: Nabil L. Muhanna, Gainesville, GA (US); Lance Middleton, Trumbull, CT (US)

(73) Assignee: Howmedica Osteonics Corp., Allendale, NJ (US); by said Lance Middleton ( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/543,288

(22) Filed: Apr. 5, 2000

Related U.S. Application Data

(60) Provisional application No. 60/127,736, filed on Apr. 5, 1999.

(51) Int. Cl.$^7$ ................................................ A61F 2/08
(52) U.S. Cl. .................................. 623/13.14; 623/13.11
(58) Field of Search ........................... 623/13.16, 13.11, 623/13.13, 13.2; 606/69

(56) References Cited

U.S. PATENT DOCUMENTS

| | | | |
|---|---|---|---|
| 4,403,606 A | 9/1983 | Woo et al. | |
| 4,403,607 A | 9/1983 | Woo et al. | |
| 4,493,317 A | 1/1985 | Klaue | |
| 4,513,744 A | 4/1985 | Klaue | |
| 4,743,260 A | * 5/1988 | Burton | 623/17 |
| 4,773,406 A | 9/1988 | Spector et al. | |
| 5,002,544 A | 3/1991 | Klaue et al. | |
| 5,019,078 A | 5/1991 | Perren et al. | |
| 5,053,036 A | 10/1991 | Perren et al. | |
| 5,116,336 A | 5/1992 | Frigg | |
| 5,147,361 A | 9/1992 | Ojima et al. | |
| 5,151,103 A | 9/1992 | Tepic et al. | |
| 5,275,601 A | 1/1994 | Gogolewski et al. | |
| 5,324,290 A | 6/1994 | Zdeblick et al. | |
| 5,344,421 A | 9/1994 | Crook | |
| 5,364,399 A | 11/1994 | Lowery et al. | |
| 5,403,136 A | 4/1995 | Mathys | |
| 5,527,311 A | 6/1996 | Proctor et al. | |
| 5,549,612 A | 8/1996 | Yapp et al. | |
| 5,562,672 A | 10/1996 | Huebner et al. | |
| 5,569,251 A | 10/1996 | Baker et al. | |
| 5,601,553 A | 2/1997 | Trebing et al. | |

(List continued on next page.)

FOREIGN PATENT DOCUMENTS

| | | |
|---|---|---|
| DE | 3914164 | 1/1991 |
| WO | 9007304 | 7/1990 |
| WO | 9851226 | 11/1998 |

*Primary Examiner*—Corrine McDermott
*Assistant Examiner*—Thomas Barrett
(74) *Attorney, Agent, or Firm*—Lerner, David, Littenberg, Krumholz & Mentlik, LLP

(57) ABSTRACT

A simple and flexible artificial ligament which easily conforms to a patient's anatomy and can be used independently or in combination with an intervertebral graft, implant or prosthesis to return stability to the spine subsequent to a surgical spinal procedure is disclosed. In one preferred embodiment, the artificial ligament is in the form of a flexible conformable plate dimensioned to span adjacent vertebrae and having openings for reception of bone screws, fasteners, etc. to mount the plate to the vertebrae. The biomechanical supporting characteristics of the plate approximate the characteristics of the ligament (e.g., anterior spinal) which it replaces thereby providing appropriate support to the spine in extension which also permitting normal spine mobility. A method of supporting adjacent vertebrae with the artificial ligament is also disclosed.

9 Claims, 5 Drawing Sheets

U.S. PATENT DOCUMENTS

| | | |
|---|---|---|
| 5,607,426 A | 3/1997 | Ralph et al. |
| 5,613,967 A | 3/1997 | Engelhardt et al. |
| 5,616,144 A | 4/1997 | Yapp et al. |
| 5,674,296 A * | 10/1997 | Bryan et al. .................. 623/17 |
| 5,681,310 A | 10/1997 | Yuan et al. |
| 5,681,311 A | 10/1997 | Foley et al. |
| 5,709,686 A | 1/1998 | Talos et al. |
| 5,733,287 A | 3/1998 | Tepic et al. |
| 5,735,853 A | 4/1998 | Olerud |
| 5,766,176 A | 6/1998 | Duncan |
| 5,772,662 A | 6/1998 | Chapman et al. |
| 5,800,433 A | 9/1998 | Benzel et al. |
| 5,807,396 A | 9/1998 | Raveh |
| 5,871,486 A | 2/1999 | Huebner et al. |
| 5,891,145 A | 4/1999 | Morrison et al. |
| 5,904,683 A | 5/1999 | Pohndorf et al. |
| 5,964,762 A | 10/1999 | Biedermann et al. |
| 6,022,350 A | 2/2000 | Ganem |
| 6,030,389 A | 2/2000 | Wagner et al. |

\* cited by examiner

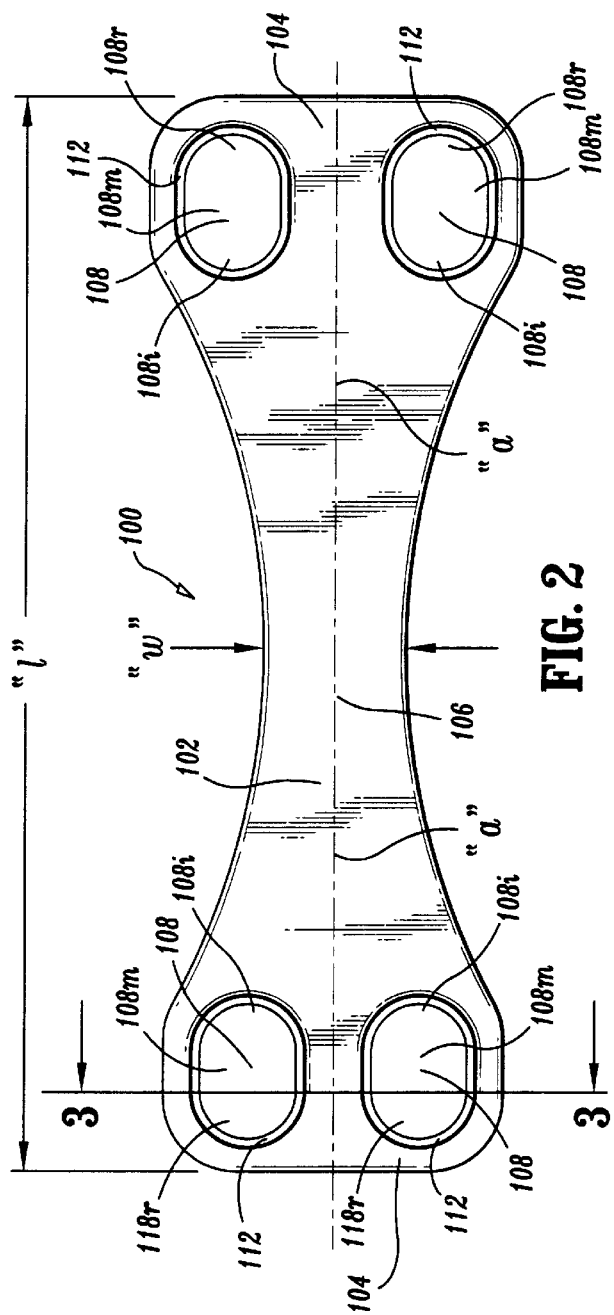

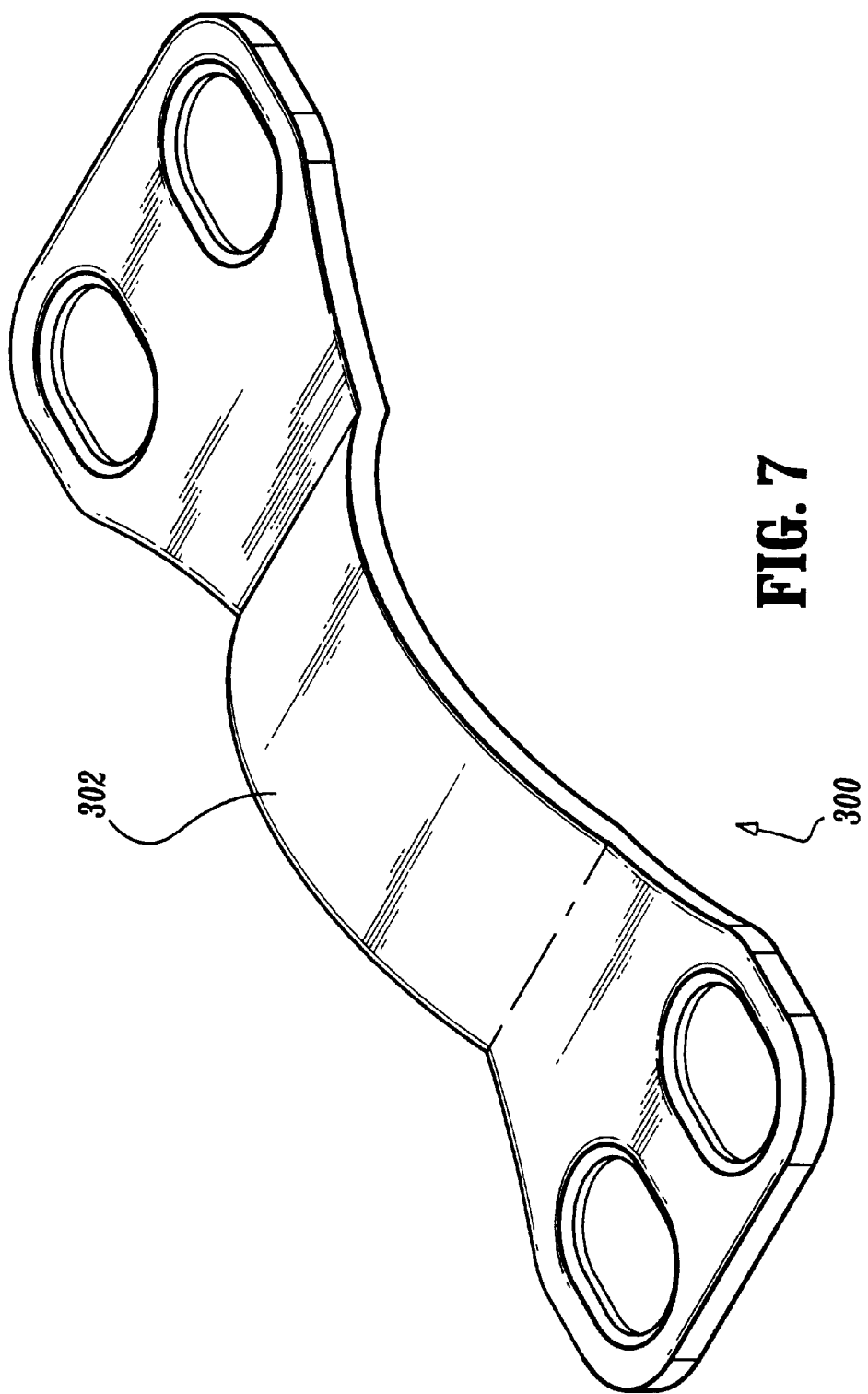

ARTIFICIAL SPINAL LIGAMENT

CROSS-REFERENCE TO RELATED APPLICATIONS

This application claims the benefit of U.S. provisional patent application Ser. No. 60/127,736, filed Apr. 5, 1999, the entire disclosure of which is hereby incorporated by reference.

BACKGROUND

1. Field of the Disclosure

The present disclosure relates generally to prosthetic members for joining or repairing bone segments, including artificial ligaments and, more specifically, to an artificial ligament intended for partial or full replacement of the anterior longitudinal ligament of the anterior lumbar, thoracic or cervical spine.

2. Discussion of the Prior Art

Ligaments extend between adjacent bone structures and serve a primary function of maintaining and providing appropriate stability to the bone structures to maintain the structures in aligned, spaced relation, particularly when subjected to loads in tension or upon torsional movement. Spinal ligaments stabilize and support vertebral bodies during movement of the spine.

During surgical treatment of the spine, a section of a spinal ligament may be resected to provide access to a diseased or damaged intervertebral disc and/or to permit introduction of a fusion implant, bone graft or intervertebral disc prosthesis intended for long term support of the vertebral bodies. The bone graft, fusion implant or intervertebral disc return stability to the spinal column in compression and flexing, however, due to removal of the spinal ligament, the biomechanical characteristics of extension and torsional stability lost by the ligament's removal must be replaced. Current techniques involve the use of metal bone plates which are secured to the vertebral bodies with screw locking mechanisms. Conventional bone plates, however, are rigid and, thus, significantly inhibit spine mobility. Additionally, the screw locking mechanisms utilized with such plates are relatively complicated and provide minimal flexibility with respect to fastener positioning, etc.

SUMMARY

Accordingly, the present disclosure is directed to a simple and flexible artificial ligament which easily conforms to a patient's anatomy and can be used independently or in combination with an intervertebral graft, implant or prosthesis. In one preferred embodiment, an artificial spinal ligament is in the form of a flexible conformable plate dimensioned to span adjacent vertebrae and having openings for reception of bone screws, fasteners, etc. to mount the plate to the vertebrae. The biomechanical supporting characteristics of the plate approximate the characteristics of the ligament (e.g., anterior spinal) which it replaces thereby providing appropriate support to the spine in extension which also permitting normal spine mobility. A method of supporting adjacent vertebrae with the artificial ligament is also disclosed.

BRIEF DESCRIPTION OF THE DRAWINGS

Preferred embodiments of the disclosure are described herein with reference to the drawings wherein:

FIG. 2 is a top plan view of the artificial ligament of FIG. 1;

FIG. 3 is a cross-sectional view taken along lines 3—3 of FIG. 2;

FIG. 7 is a perspective view of another alternate embodiment of the artificial ligament.

DETAILED DESCRIPTION OF PREFERRED EMBODIMENTS

Figure 1:
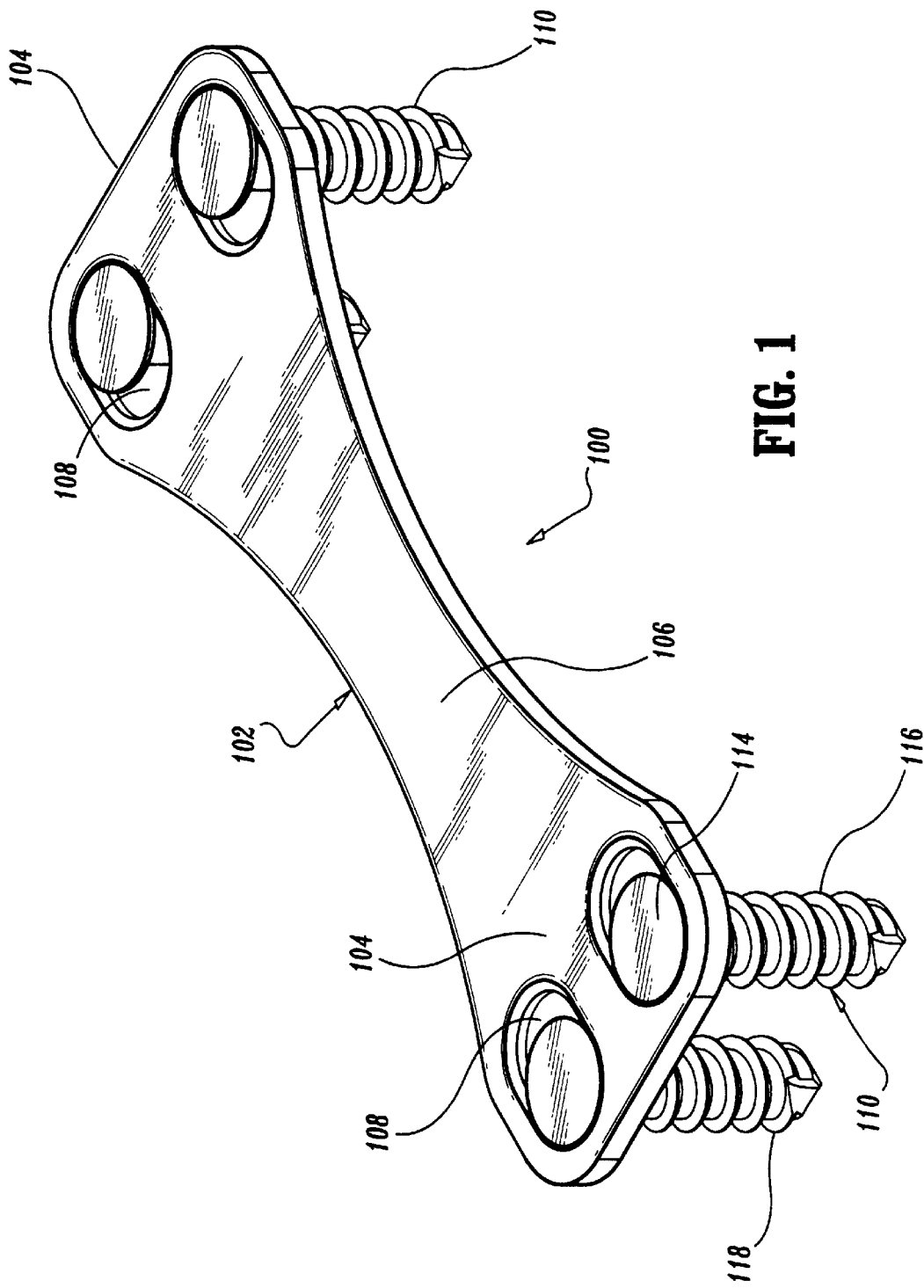
FIG. 1 is a perspective view of the artificial ligament of the present disclosure.

Referring now to the drawings, in which like reference numerals identify similar or identical elements throughout the several views, there is illustrated the artificial ligament of the present disclosure. The artificial ligament of the present disclosure is intended to replace part or all of the supporting function of a ligament previously removed in connection with a surgical procedure. The artificial ligament has particular application in replacing the supportive function of a spinal ligament, e.g., anterior or posterior, which may have been fully or partially resected during a spinal procedure. The artificial ligament is advantageously dimensioned to be positioned to span adjacent vertebrae to restore the natural biomechanics, e.g., including tensional support and range of motion, of the removed ligament segment. The artificial ligament is contemplated for use with a bone graft, fusion implant or artificial disc to compliment the compressive load characteristics of the implant with its tensional supporting capabilities during healing. It is also envisioned that the ligament may be utilized in other capacities such as, for example, repair of other body ligaments such as the anterior crucial ligament, etc.

Referring initially to FIGS. 1–3, artificial ligament 100 includes ligament body or plate 102 which is advantageously dimensioned to span at least two adjacent vertebrae. It is envisioned that the ligament body 102 may span three or more vertebral bodies. In a preferred embodiment, the length "l" of ligament body 102 ranges from about 1–3 inches, preferably about 2 inches.

Ligament body 102 is preferably fabricated from a generally flexible material. The selected flexible material of ligament body 102 preferably has physical characteristics which approximate the biomechanical characteristics of the spinal ligament which it replaces. More specifically, the selected material of ligament body 102 supports the spine and provides stability in extension, i.e., the ligament body has tensional load bearing capabilities while also permitting a degree of flexibility approximating the natural ligament. A preferred material of fabrication for ligament body 102 includes a flexible polymeric material such as polyethylene.

Ligament body 102 defines first and second web body end portions 104 connected through intermediate body portion 106. Web body end portions 104 each include a pair of apertures 108 for reception of bone fasteners 110. As best depicted in FIG. 2, apertures 108 may be generally elongated or slotted in the longitudinal direction with respect to longitudinal axis "a" of body 102 to permit multi-position capabilities of the bone fasteners 110 with respect to ligament body 102 and the vertebral bodies as will be discussed. Apertures 108 are preferably countersunk defining a beveled or chamfered surface 112 adjacent the upper surface of the ligament body 102 for reception of the head 114 of the bone fasteners 110 in flush relation therewith. Although two apertures 108 are shown in each web end portion 104 of the preferred embodiment, it is envisioned that each web portion 104 may have more than two apertures or only one aperture.

With particular reference to FIG. 2, intermediate body portion 106 has a width "w" which is substantially less than the corresponding width of web portion 104. Such dimensioning reduces the transverse profile of ligament body 102 thereby increasing flexibility to facilitate torsional movement of ligament body 102 upon corresponding movement of the patient's spine. The width "w" of intermediate body portion 102 ranges from about 0.125 inches to about 0.375 inches, more preferably, about 0.250 inches.

With reference again to FIG. 1, bone fasteners 110 serve as anchoring means for securing the ligament body 102 to the adjacent vertebrae. The preferred bone fastener 110 includes a fastener head 114 and a fastener shaft 116 extending from the fastener head. The fastener shaft 116 is threaded preferably with a self-tapping thread 118. Upon mounting of bone fastener 110 within the adjacent vertebrae, the fastener head 114 is preferably flush with the upper surface of the ligament body 102. Other anchoring means for mounting ligament body 102 to the vertebral bodies are envisioned by one skilled in the art including expandable bolts, screws, non-threaded fasteners, etc.

In use in connection with an anterior spinal procedure, the anterior ligament is removed to permit access to a diseased or damaged disc section. A partial or full discectomy may be performed followed by insertion of a bone graft, fusion implant (e.g., as disclosed in U.S. Pat. No. 4,961,740, the contents of which are incorporated herein by reference) or an intervertebral prosthesis (such as disclosed in commonly assigned application Ser. No. 09/098,606, filed Jun. 17, 1998, the contents of which are incorporated herein by reference).

When used with fusion devices, the bone fasteners 110 are placed at the outer area 108r of the openings 108 so the ligament is rigid in tension while allowing for compression. This provides for immediate stability in extension as extension loads immediately place the ligament in tension. The fasteners 110 are free to move within openings 108 relative to the ligament 102 in compression. This also permits graft compression.

When used with artificial discs, the fasteners 110 are placed in the middle 108m or inner part 168i of the openings 108 to permit limited relative motion of fasteners 110 within openings 108 of the ligament in both flexion and extension. Extension ultimately leads to tension in the ligament as the fasteners 110 meet the ends 108r of the openings 108. Thus, movement in tension and compression is provided. This flexibility also reduces the likelihood of the fasteners 110 backing out over time.

Figure 4:
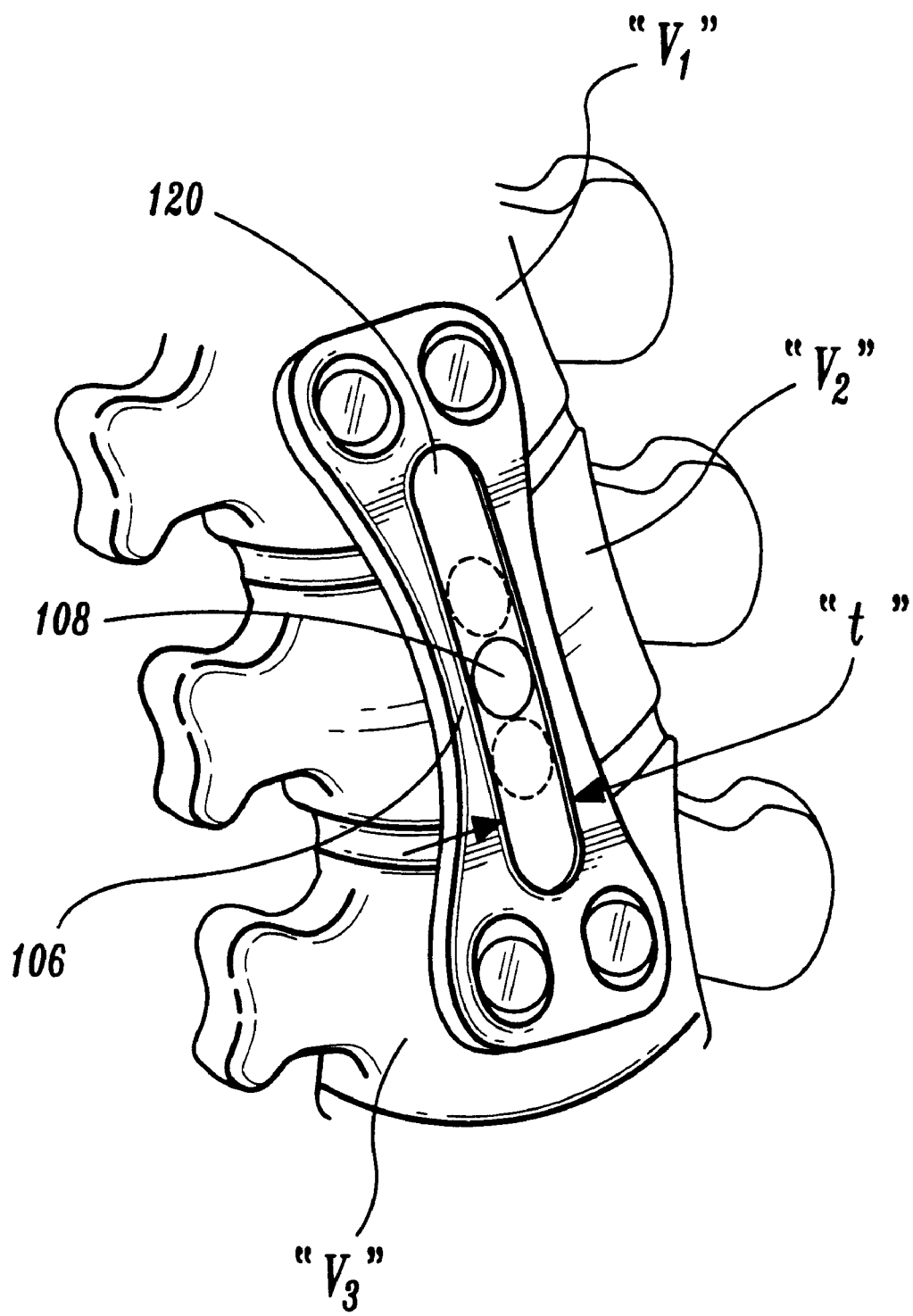
FIG. 4 is a perspective view of an alternate embodiment illustrating mounting thereof to the vertebral column.

FIG. 4 illustrates an alternate embodiment of the artificial ligament where intermediate body portion 106 includes an elongated longitudinal depression 120 defining a reduced thickness of ligament body 102. This reduced thickness permits the surgeon to create an additional opening 108 in the ligament body 102 to receive a bone fastener 110 for further fixation to the vertebrae. More specifically, during the surgical procedure the surgeon may create an opening at a desired location within intermediate body portion 106 with a punch or the like. A multitude of openings (shown in phantom) may be formed within depression 120. This feature facilitates use of ligament body 102 in spanning more than two vertebrae, e.g., three vertebrae. FIG. 4 illustrates this embodiment mounted to the spinal column and spanning three (3) vertebral portions "$v_1$–$v_3$" with the middle opening 108 having a fastener for attachment to the intermediate vertebrae "$v_2$" and the outer openings 108 having fasteners 110 mounted to respective vertebrae "$v_1$", "$v_3$". Depression 120 preferably also defines a transverse dimension "t" which approximates the diameter of the fastener head 114 to facilitate retention of the head with respect to the ligament body 102.

Figure 6:
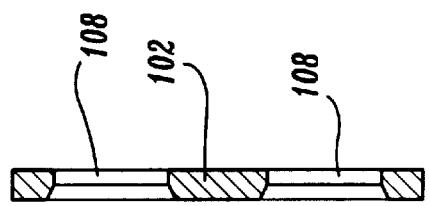
FIG. 6 is a cross-sectional view taken along lines 6—6 of FIG. 5.
Figure 5:
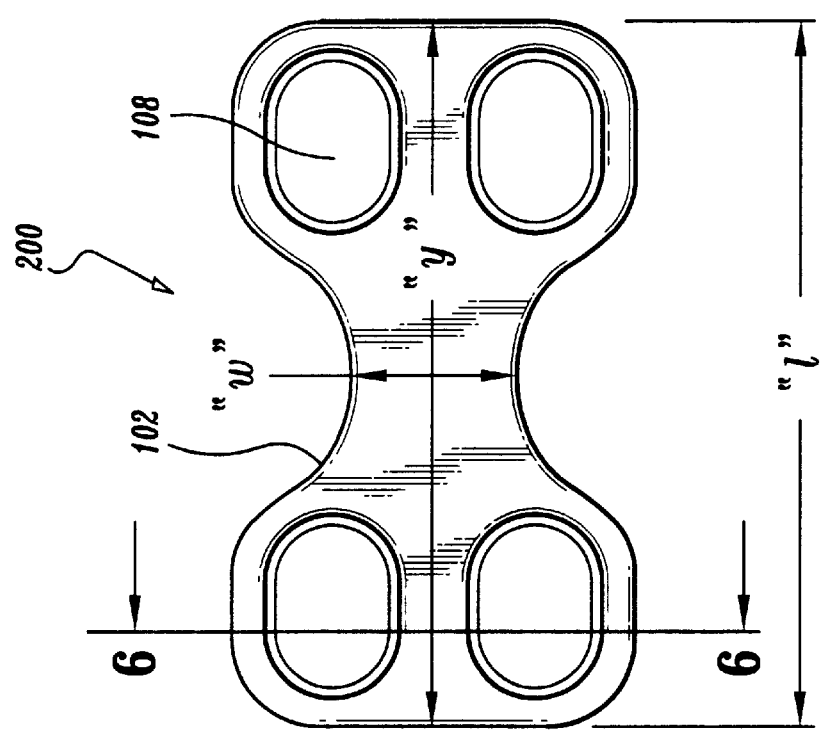
FIG. 5 is a top plan view of an alternate embodiment of FIG. 1.

FIGS. 5 and 6 illustrate an alternate embodiment of the artificial ligament 100 of FIG. 1. Artificial ligament 200 is substantially similar to the ligament 100, but, differs primarily in its dimensioning. More specifically, the length "l" of ligament body 102 is shorter than the length "l" of the embodiment of FIG. 1, preferably ranging in length from about 0.75–1.25 inches, more preferably about 1.14 inches. In all other respects, the ligament 200 is identical to ligament 100 of FIG. 1.

FIG. 7 illustrates another alternate embodiment of the ligament of the present disclosure. Ligament 300 includes a slight arcuate bend 302 or bump adjacent its intermediate portion. The arcuate bend provides a degree of excess material to permit the effective length of the ligament to increase when ligament 300 is placed in tensioned, i.e., the arcuate bend will tend to straighten under extension. The ligament 300 will become increasingly stiffer with a higher tension load. Multiple bends are also envisioned to establish non-linear stiffness.

While the above description contains many specifics, these specifics should not be construed as limitations on the scope of the disclosure, but merely as exemplifications of preferred embodiments thereof. For example, the present prosthetic device disclosed herein may be implanted to repair a variety of bone structures such as the ankle, knee, wrist, etc. Those skilled in the art will envision many other possible variations that are within the scope and spirit of the disclosure.

What is claimed is:

1. A flexible prosthesis for supporting adjacent vertebrae, which comprises:

a flexible elongated plate member defining a longitudinal axis and having a length sufficient to at least span an intervertebral space between adjacent vertebrae, the flexible elongate plate member comprising a material having physical characteristics approximating the natural biomechanical characteristics of a spinal ligament to thereby permit the plate member to provide support to the adjacent vertebrae when subjected to a load in tension while permitting a degree of torsional movement about the longitudinal axis when subjected to a load in torsion, the flexible elongate plate member defining oppositely oriented longitudinal end portions, each end portion having at least two slotted apertures extending therethrough, and an intermediate portion disposed between the longitudinal end portions, the intermediate portion defining a width substantially less than corresponding widths of the longitudinal end portions and having an area of reduced thickness to facilitate torsional movement of the plate member, and a fastener inserted into the at least one of the at least two slotted apertures of each longitudinal end portion for mounting the plate member to the adjacent vertebrae.

2. The flexible prosthesis according to claim 1 wherein the material of the plate member is a polymeric material.

3. The flexible prosthesis according to claim 1 wherein the polymeric material is a polyethylene.

4. The flexible prosthesis according to claim 1 wherein at least one of the at least two slotted apertures is generally elongated in a longitudinal direction with respect to the longitudinal axis of the plate member to permit movement of the plate member relative to the respective first or second fastener.

5. The flexible prosthesis according to claim 1 wherein the plate member is configured to be non-load bearing in compression.

6. The flexible prosthesis according to claim 1 wherein the plate member is a monolithically formed single unit.

7. The flexible prosthesis according to claim 1 wherein the intermediate portion includes an arcuate bend, the arcuate bend being configured to deform toward a linear configuration upon application of a threshold tensional load to the plate member.

8. The flexible prosthesis according to claim 7 wherein the plate member is a monolithically formed single unit.

9. A flexible prosthesis for supporting adjacent vertebrae, which comprises:

a flexible elongate plate member defining a longitudinal axis and having a length sufficient to at least span an intervertebral space between adjacent vertebrae, the flexible elongate plate member comprising a material having physical characteristics approximating the natural biomechanical characteristics of a spinal ligament to thereby permit the plate member to provide support to the adjacent vertebrae when subjected to a load in tension while permitting a degree of torsional movement about the longitudinal axis when subjected to a load in torsion, the flexible elongate plate member defining oppositely oriented longitudinal end portions, each end portion having at least two slotted apertures extending therethrough, and an intermediate portion disposed between the longitudinal end portions, the intermediate portion defining an arcuate bend configured to deform toward a liner arrangement upon application of a threshold tensional load to the plate member, the intermediate portion having a width substantially less than corresponding widths of the longitudinal end portions, and a fastener inserted into the at least one of the at least two slotted apertures of each longitudinal end portion for mounting the plate member to the adjacent vertebrae.

* * * * *

UNITED STATES PATENT AND TRADEMARK OFFICE
CERTIFICATE OF CORRECTION

PATENT NO. : 6,585,769 B1  
DATED : July 1, 2003  
INVENTOR(S) : Nabil L. Muhanna and Lance Middleton It is certified that error appears in the above-identified patent and that said Letters Patent is hereby corrected as shown below:

Title page,
Item [60], Related U.S. Application Data, "60/127,736" should read
-- 60/127,735 --.

Column 1,
Line 6, "60/127,736" should read -- 60/127,735 --.

Column 3,
Line 46, "168" should read -- 180 --.

Column 4,
Line 60, after "into", delete "the" (second occurrence).

Column 6,
Line 14, "liner" should read -- linear --.
Line 18, after "into" delete "the".

Signed and Sealed this

Twenty-fifth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,585,769 B1
DATED : July 1, 2003
INVENTOR(S) : Nabil L. Muhanna and Lance Middleton It is certified that error appears in the above-identified patent and that said Letters Patent is hereby corrected as shown below:

Title page,
Item [60], Related U.S. Application Data, "60/127,736" should read
-- 60/127,735 --.

Column 1,
Line 6, "60/127,736" should read -- 60/127,735 --.

Column 3,
Line 46, "168" should read -- 108 --.

Column 4,
Line 60, after "into", delete "the" (second occurrence).

Column 6,
Line 14, "liner" should read -- linear --.
Line 18, after "into" delete "the".

This certificate supersedes Certificate of Correction issued November 25, 2003.

Signed and Sealed this

Seventeenth Day of February, 2004

JON W. DUDAS
*Acting Director of the United States Patent and Trademark Office*